United States Patent
Jenson et al.

(10) Patent No.: US 10,314,608 B2
(45) Date of Patent: Jun. 11, 2019

(54) THROMBECTOMY APPARATUS AND METHOD

(71) Applicant: BOSTON SCIENTIFIC SCIMED, INC., Maple Grove, MN (US)

(72) Inventors: Mark L. Jenson, Greenfield, MN (US); William J. Drasler, Minnetonka, MN (US); Joseph M. Thielen, Buffalo, MN (US)

(73) Assignee: BOSTON SCIENTIFIC SCIMED INC., Maple Grove, MN (US)

( * ) Notice: Subject to any disclaimer, the term of this patent is extended or adjusted under 35 U.S.C. 154(b) by 38 days.

(21) Appl. No.: 15/497,357

(22) Filed: Apr. 26, 2017

(65) Prior Publication Data

US 2017/0224374 A1  Aug. 10, 2017

Related U.S. Application Data

(63) Continuation of application No. 14/513,579, filed on Oct. 14, 2014, now Pat. No. 9,662,137, which is a continuation of application No. 12/040,179, filed on Feb. 29, 2008, now Pat. No. 8,900,179, which is a
(Continued)

(51) Int. Cl.
*A61B 17/3203* (2006.01)
*A61B 17/221* (2006.01)
*A61F 2/01* (2006.01)
*A61M 1/00* (2006.01)
(Continued)

(52) U.S. Cl.
CPC ...... *A61B 17/32037* (2013.01); *A61B 17/221* (2013.01); *A61F 2/013* (2013.01); *A61M 1/008* (2013.01); *A61M 25/01* (2013.01); *A61M 25/09* (2013.01); *A61B 2017/2212* (2013.01); *A61M 2025/0183* (2013.01)

(58) Field of Classification Search
CPC ...... A61M 1/008; A61M 25/01; A61M 25/09; A61B 17/32037; A61B 17/221
See application file for complete search history.

(56) References Cited

U.S. PATENT DOCUMENTS

| | | |
|---|---|---|
| 1,144,268 A | 6/1915 | Vickery |
| 1,148,093 A | 7/1915 | Kells |
| 4,638,539 A | 1/1987 | Palmer |

(Continued)

FOREIGN PATENT DOCUMENTS

| | | |
|---|---|---|
| DE | 3715418 A1 | 11/1987 |
| EP | 1488748 A1 | 12/2004 |

(Continued)

*Primary Examiner* — Edelmira Bosques
(74) *Attorney, Agent, or Firm* — Seager, Tufte & Wickhem LLP.

(57) ABSTRACT

A thrombectomy system may include an elongate shaft that defines a high pressure lumen and a low pressure lumen. The high pressure lumen may terminate near an end of the low pressure lumen. An expandable capture basket may be disposed near the end of the low pressure lumen. A thrombectomy apparatus may include an elongate shaft, an evacuation lumen extending within the elongate shaft and a high pressure lumen extending within the elongate shaft. A capture apparatus may be disposed within a wire lumen that extends within the elongate shaft such that the capture apparatus extends distally from the wire lumen.

16 Claims, 16 Drawing Sheets

Related U.S. Application Data continuation of application No. 12/026,317, filed on Feb. 5, 2008, now Pat. No. 8,430,837.

(60) Provisional application No. 60/888,265, filed on Feb. 5, 2007.

(51) Int. Cl.
*A61M 25/01* (2006.01)
*A61M 25/09* (2006.01)

(56) References Cited

U.S. PATENT DOCUMENTS

| | | | |
|---|---|---|---|
| 4,690,672 A | 9/1987 | Veltrup | |
| 5,057,098 A | 10/1991 | Zelman | |
| 5,135,482 A | 8/1992 | Neracher | |
| 5,248,297 A | 9/1993 | Takase | |
| 5,318,518 A | 6/1994 | Plechinger et al. | |
| 5,370,609 A * | 12/1994 | Drasler | A61B 17/32037 604/22 |
| 5,395,315 A | 3/1995 | Griep | |
| 5,419,772 A | 5/1995 | Teitz et al. | |
| 5,496,267 A * | 3/1996 | Drasler | A61B 17/32037 604/22 |
| 5,606,968 A | 3/1997 | Mang | |
| 5,713,851 A | 2/1998 | Boudewijn et al. | |
| 5,795,332 A | 8/1998 | Lucas et al. | |
| 5,827,229 A | 10/1998 | Auth et al. | |
| 5,989,210 A | 11/1999 | Morris et al. | |
| 6,022,336 A | 2/2000 | Zandna-Azizi et al. | |
| 6,096,001 A | 8/2000 | Drasler et al. | |
| 6,129,697 A | 10/2000 | Drasler et al. | |
| 6,129,698 A | 10/2000 | Beck | |
| 6,224,570 B1 | 5/2001 | Le et al. | |
| 6,375,635 B1 | 4/2002 | Moutafis et al. | |
| 6,544,209 B1 | 4/2003 | Drasler et al. | |
| 6,572,578 B1 | 6/2003 | Blanchard | |
| 6,579,270 B2 | 6/2003 | Sussman et al. | |
| 6,616,679 B1 | 9/2003 | Khorsavi et al. | |
| 6,635,070 B2 | 10/2003 | Leeflang et al. | |
| 6,719,717 B1 | 4/2004 | Johnson et al. | |
| 6,755,803 B1 | 6/2004 | Le et al. | |
| 6,926,726 B2 | 8/2005 | Drasler et al. | |
| 7,846,175 B2 | 12/2010 | Bonnette et al. | |
| 2002/0068895 A1 | 6/2002 | Beck | |
| 2002/0173819 A1 | 11/2002 | Leeflang et al. | |
| 2003/0144688 A1 | 7/2003 | Brady et al. | |
| 2003/0216760 A1 | 11/2003 | Welch et al. | |
| 2004/0193046 A1 | 9/2004 | Nash et al. | |
| 2004/0199201 A1 | 10/2004 | Kellet et al. | |
| 2004/0243157 A1 | 12/2004 | Connor et al. | |

FOREIGN PATENT DOCUMENTS

| | | |
|---|---|---|
| JP | 6205785 A | 7/1994 |
| JP | 2001161700 A | 6/2001 |
| JP | 20030101194 A | 1/2003 |
| WO | 2004100772 A2 | 11/2004 |

* cited by examiner

THROMBECTOMY APPARATUS AND METHOD

RELATED APPLICATIONS

This application is a continuation of U.S. application Ser. No. 14/513,579, filed Oct. 14, 2014, which is a continuation of U.S. application Ser. No. 12/040,179 filed Feb. 29, 2008, which is a continuation of U.S. application Ser. No. 12/026,317, filed Feb. 5, 2008, now U.S. Pat. No. 8,430,837, which claims priority to U.S. Provisional Application No. 60/888,265 filed Feb. 5, 2007.

TECHNICAL FIELD

The present invention pertains generally to medical devices and methods of their use. More particularly, the present invention pertains to thrombectomy devices and methods of their use.

BACKGROUND

A variety of methods have been developed to remove thrombi and other unwanted material from a patient's vasculature. Examples include thrombolytic medications and mechanical devices such as fluid jets, ultrasound, laser, thermal, suction, balloons, rotating burrs, cutters, baskets, and wires. Thrombolytic medications are simpler to administer and have advantages in reaching any desired vessel, but disadvantages in slower action, monitoring requirements, bleeding complications, high cost, inability to remove harder or more organized thrombi, and travel to other vessels besides the target vessel. Mechanical devices are often faster and are specific to the target vessel, but have disadvantages in being larger size, difficulty in reaching a target vessel, local injury to the vessel wall, mechanical plugging, complicated and time-consuming setup, complicated operation requiring operator training and skill, and high cost; the effectiveness on harder or more organized thrombi varies, with the more effective devices being more invasive, more dangerous, or more expensive.

There are many situations in which it is desirable to remove thrombus or blood clots from the body, particularly in large blood vessels, heart chambers, or in extravascular spaces which could fill with blood during hemorrhage such as retroperitoneal bleeding, or other spaces such as cerebrospinal fluid spaces, hollow body organs, and so forth.

Existing thrombectomy devices, including fluid jet thrombectomy devices, have difficulty in treating large thrombi and in efficiently and effectively removing thrombus from large diameter vessels. A fluid Jet catheter may obtain some mixing and work at some distance, but doing so safely and capturing all the thrombus for removal is problematic. A variety of thrombus removal catheters can be utilized in smaller vessels such as coronary or leg arteries, and so forth.

Thus, a need remains for improved thrombus removal capability particularly for large vessels, including peripheral or central veins, pulmonary arteries and branches, chambers of the heart, larger arteries, and vascular prostheses.

SUMMARY

The invention pertains generally to devices for removing thrombi and other unwanted materials from within vessels such as relatively large arteries and veins. In an illustrative but non-limiting example, a thrombectomy system may include an elongate shaft that defines a high pressure lumen and a low pressure lumen. The high pressure lumen may terminate near an end of the low pressure lumen. An expandable capture basket may be disposed near the end of the low pressure lumen. In some applications, the thrombectomy system may function without a capture basket.

In another illustrative but non-limiting example, a thrombectomy apparatus may include an elongate shaft, an evacuation lumen extending within the elongate shaft and a high pressure lumen extending within the elongate shaft. A capture apparatus may be disposed within a wire lumen that extends within the elongate shaft such that the capture apparatus extends distally from the wire lumen.

In another illustrative but non-limiting example, an apparatus may include a first catheter shaft segment and a second catheter shaft segment. The first catheter shaft segment may have a suction lumen and a high pressure lumen. The second catheter shaft segment may have a wire lumen and a capture apparatus that is disposed at least partially within the wire lumen.

In another illustrative but non-limiting example, thrombi may be removed from within a vessel by using a high pressure jet as an ejector/aspiration device to pull the thrombi within the suction lumen. The captured thrombi may be disrupted by the high pressure jet and the disrupted thrombi may be suctioned out of the vessel. In such apparatus, the high pressure jet may be located near the distal opening of the distal tip. In some embodiments, the high pressure jet may exit a high pressure lumen at an angle which generally parallels a proximal slope associated with the distal opening or at an angle which is somewhat more inclined toward an axial orientation.

In another illustrative but non-limiting example, thrombi may be removed from within a vessel by capturing the thrombi within a capture apparatus. The captured thrombi may be disrupted with a high pressure jet and then the disrupted thrombi may be suctioned out of the vessel.

In another illustrative but non-limiting example, thrombi may be removed by providing a thrombectomy apparatus similar to that described above. The thrombectomy apparatus may be advanced to a desired location within a patient's vasculature. The expandable capture basket may be expanded, and thrombi may be captured therein. A high pressure fluid source may be provided via the high pressure lumen in order to break apart the captured thrombi. Suction may be applied to the low pressure lumen in order to evacuate the broken apart thrombi.

The above summary of some embodiments is not intended to describe each disclosed embodiment or every implementation of the present invention. The Figures and Detailed Description that follow more particularly exemplify these embodiments.

BRIEF DESCRIPTION OF THE FIGURES

The invention may be more completely understood in consideration of the following detailed description of various embodiments of the invention in connection with the accompanying drawings, in which.

Figure 1:
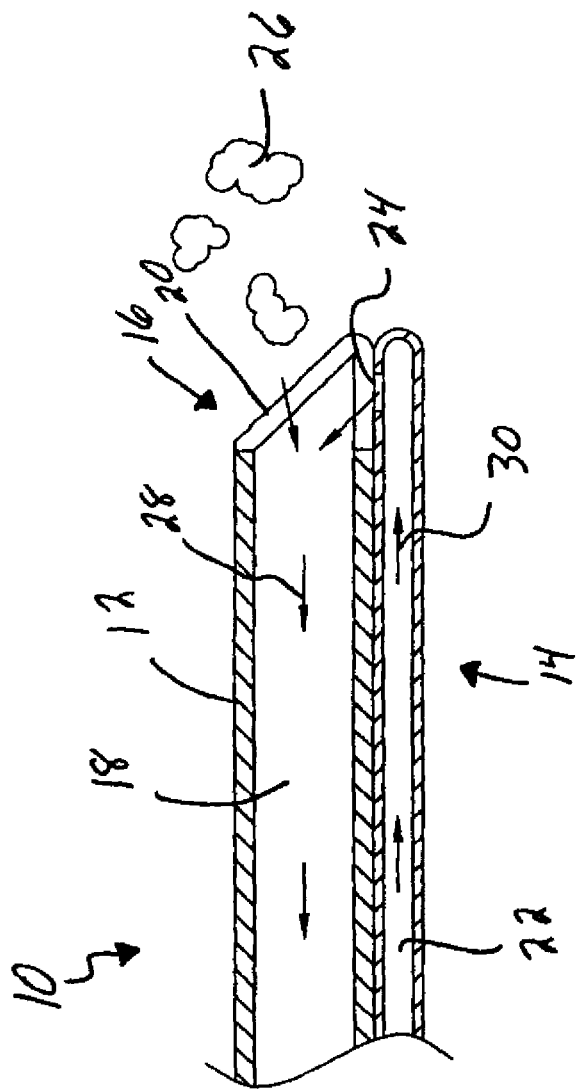
FIG. 1 is a diagrammatic view of a portion of a thrombectomy apparatus in accordance with an embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

The invention pertains generally to a thrombectomy apparatus that includes a low pressure or evacuation lumen, a high pressure lumen and an expandable capture basket. In some cases, a thrombectomy apparatus may be provided within an external sheath for storage, transportation and/or delivery.

Merely for clarity, some Figures show only certain elements of the invention while not showing certain other elements. It will be understood that these elements may be combined as desired in practicing the invention.

FIG. 1 is a schematic cross-sectional view of a portion of a thrombectomy catheter 10. The thrombectomy catheter 10 includes an elongate shaft 12 that has a distal region 14 defining a distal end 16. In the illustrated embodiment, a low pressure or evacuation lumen 18 extends through the distal region 12 and may, as shown, extend to the distal end 14. The evacuation lumen 18 may terminate at a distal opening 20. A high pressure lumen 22 may extend through the distal region 14. The high pressure lumen 22 may terminate at a distal opening 24.

In some instances, as illustrated, the high pressure lumen 22 may extend at least substantially parallel with the evacuation lumen 18. In some cases, the high pressure lumen 22 may be formed by a tubular member extending within the evacuation lumen 18. While not expressly shown in this Figure, it will be recognized that the elongate shaft 12 may include one or more additional lumens such as a capture basket lumen, a guidewire lumen, and the like.

In FIG. 1, the thrombectomy catheter 12 may be considered as being disposed within a patient's vasculature or other desired lumen or void that may contain thrombi or other undesirable material, although the environment is not expressly shown. Thrombi 26 are generically shown disposed just distal of the distal end 16 of the elongate shaft 12. Thrombi 26 may be drawn towards and into the evacuation lumen 18 by applying a low pressure source to a proximal end (not illustrated) of the evacuation lumen 18. A low pressure source may provide suction, such as a vacuum source. The low pressure within the evacuation lumen 18 may be generically represented by arrows 28. These arrows 28 also indicate the direction in which the thrombi 26 will travel through the evacuation lumen 18.

In some cases, if desired, a high pressure fluid source may be placed in fluid communication with the high pressure lumen 22. A suitable fluid such as saline or another therapeutically acceptable fluid may travel in a direction indicated by arrows 30. In some instances, the high pressure fluid may exit the high pressure lumen 22 through the distal opening 24. In some cases, the distal opening 24 may be a jet orifice that causes the high pressure fluid to exit therefrom at a high rate of speed. The high pressure fluid may, therefore, impact the thrombi 26 and at least partially break the thrombi 26 into smaller pieces that may better fit through the evacuation lumen 18 without clogging the evacuation lumen 18.

In some cases, as illustrated, the distal opening 24 of the high pressure lumen 22 may be positioned relative to the distal opening 20 of the evacuation lumen 18 such that the high pressure fluid creates a jet that extends at least partially across the distal opening 20. As will be discussed with respect to subsequent Figures, the distal opening 24 may have a variety of different locations relative to the distal opening 20 of the evacuation lumen 18.

The elongate shaft 12 may be formed of any suitable materials. In some cases, the elongate shaft 12 may be formed of one or more suitable polymeric materials. Examples of suitable polymers include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

In some cases, the evacuation lumen 18 and the high pressure lumen 22 may be formed as parallel lumens within a single catheter shaft. In some cases, the evacuation lumen 18 may be formed within a catheter shaft or as a separate elongate tubular member while the high pressure lumen 22 may be formed as an elongate tube provided at least partially on the exterior of the catheter shaft or elongate tubular member forming the evacuation lumen 18.

Figure 2:
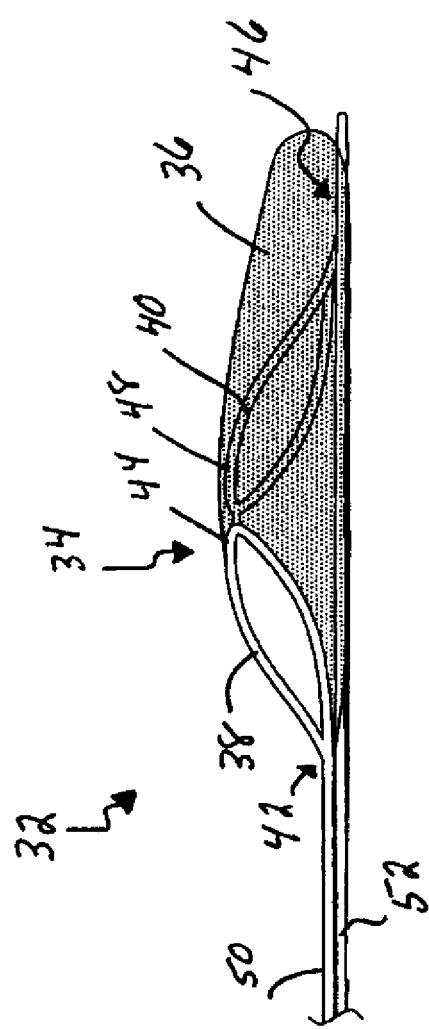
FIG. 2 is a diagrammatic view of a portion of a thrombectomy apparatus in accordance with an embodiment of the invention.

As discussed above, a thrombectomy apparatus may also include a capture basket. FIG. 2 illustrates an expandable capture basket 32 that may, if desired, be used in conjunction with or even incorporated into the thrombectomy catheter 10 discussed with respect to FIG. 1. The expandable capture basket 32 includes a frame structure 34 and a membrane 36 that is disposed over at least a portion of the frame structure 34. In some cases, the membrane 36 may be formed of any suitable material such as those listed above and may be manipulated to have any desired level of porosity. In some cases, the membrane 36 may be constructed to be at least substantially permeable to blood but not to larger items such as thrombi. In some instances, it may be useful to construct the membrane 36 to be at least substantially impermeable to blood flow.

In some cases, the frame structure 34 may include a first loop 38 and a second loop 40. The first loop 38 may have a proximal end 42 and a distal end 44 while the second loop 40 may have a distal end 46 and a proximal end 48. It will be recognized that the first loop 38 may be formed by looping a first length of wire or filament and thus the proximal end 42 may include two wire or filament ends. Similarly, the second loop 40 may be formed by looping a second length of wire or filament and thus the distal end 46 may include two wire or filament ends. In some cases, it is contemplated that the first loop 38 and/or the second loop 40 may instead be formed by welding or otherwise joining together the two ends of the first length of wire or filament to form a closed loop.

Figure 3:
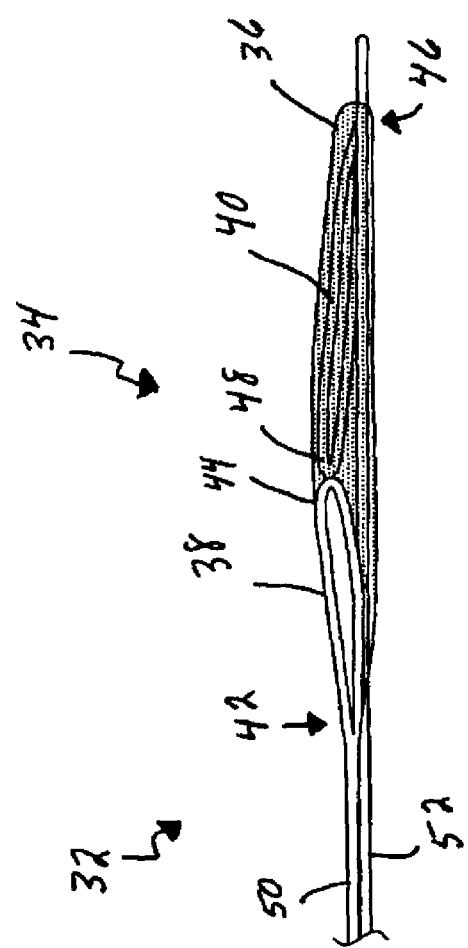
FIG. 3 is a diagrammatic view of a portion of a thrombectomy apparatus in accordance with an embodiment of the invention.
Figure 4:
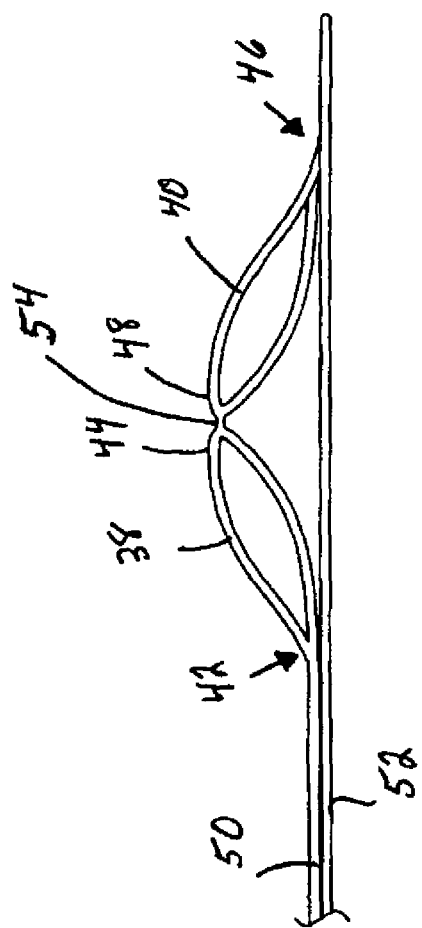
FIG. 4 is a diagrammatic view of a portion of a thrombectomy apparatus in accordance with an embodiment of the invention.

In some instances, the distal end 44 of the first loop 38 may, if desired, be secured to the proximal end 48 of the second loop 40. In some cases, the proximal end 42 of the first loop 38 may extend to and be secured to an actuation filament 50 while the distal end 46 of the second loop 40 may extend to and be secured to a wire 52. It can be seen that the expandable capture basket 32 may be either opened or closed, as desired, by axially moving the actuation filament 50 relative to the wire 52. FIG. 2 shows the expandable capture basket 32 in an open configuration while FIG. 3 shows the expandable capture basket 32 in a closed configuration. FIG. 4 provides a better view of the frame structure 34, as the membrane 36 has been removed.

It will be recognized that structure may be provided to permit the actuation filament 50 to move axially relative to the wire 52 while constraining the actuation filament 50 and/or the wire 52 from excessive radial movement. In some cases, relative movement between the actuation filament 50 and the wire 52 may be controlled by providing at least one of the actuation filament 50 and/or the wire 52 within an appropriate lumen within the thrombectomy catheter 10 (FIG. 1). In some instances, a suitable lumen may be provided either parallel to or even within the evacuation lumen 18, for example.

The actuation filament 50 and the wire 52 may be formed of any suitable material. In some cases, the actuation filament 50 and the wire 52 may, independently, be formed of any suitable polymeric or metallic material. Examples of suitable materials include metal, metal alloy, polymer (some examples of which are disclosed above), a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL®400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

As noted above, in some cases the actuation filament 50 and the wire 52 are wire structures. In some instances, however, part or all of the actuation filament 50 and/or the wire 52 may be hollow and may be in fluid communication with a high pressure fluid source such as the high pressure lumen 22 (FIG. 1). In some situations, it may be desirable to have one or more high pressure jets disposed at one or more locations within the frame structure 34. For example, it may be desirable to have a high pressure jet located at a midpoint 54 of the frame structure 34. In some cases, it may be desirable to have one or more high pressure jets disposed along the first loop 38 and/or the second loop 40. In some cases, it is contemplated that the actuation filament 50 and the wire 52 may be wire structures while another feed line (not seen in this Figure) provides fluid to the aforementioned high pressure jets.

Figure 5:
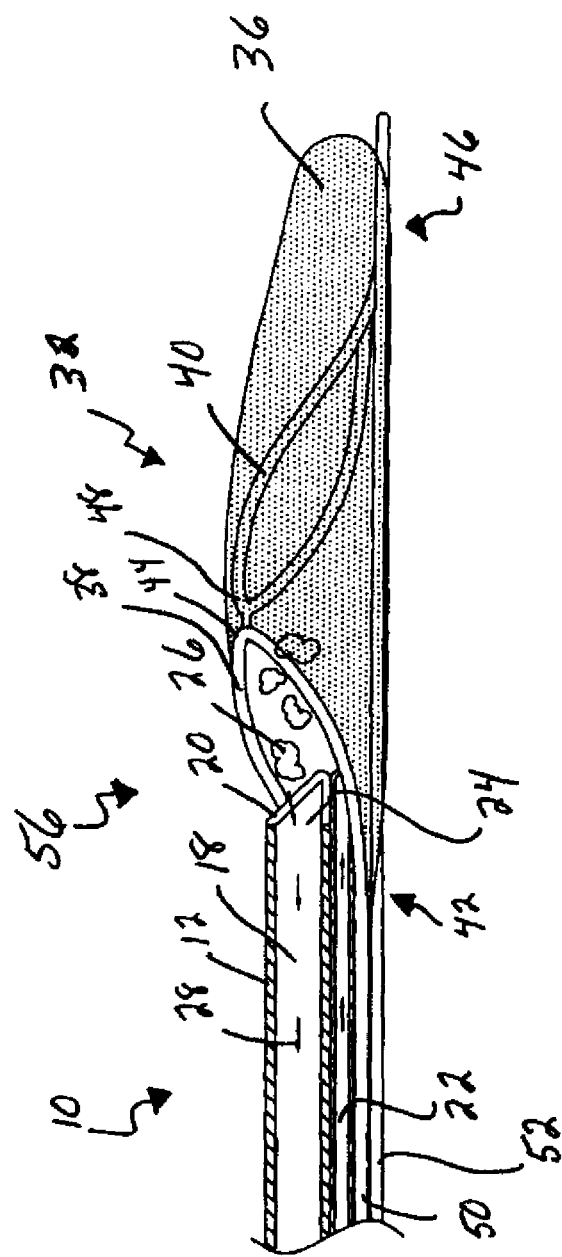
FIG. 5 is a diagrammatic view of a portion of a thrombectomy apparatus in accordance with an embodiment of the invention.

Turning now to FIG. 5, a thrombectomy assembly 56 is shown as including the thrombectomy catheter 10 and the expandable capture basket 32 as previously described. As illustrated, the actuation filament 50 and the wire 52 are shown extending proximally next to the elongate shaft 12. It will be recognized that the elongate shaft 12 may include one or more additional lumens (not illustrated) through which the actuation filament 50 and/or the wire 52 may extend. In some cases, a separate catheter (not shown) may provide a lumen or lumens suitable to constrain the actuation filament 50 and/or the wire 52.

Figure 5A:
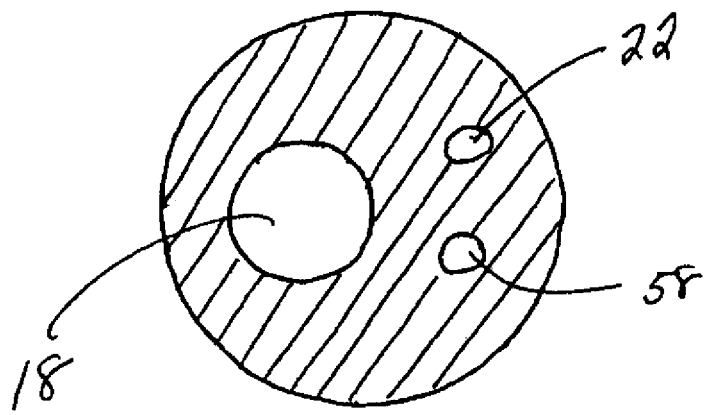
FIG. 5A is a diagrammatic view of a portion of a thrombectomy apparatus in accordance with an embodiment of the invention.
Figure 5B:
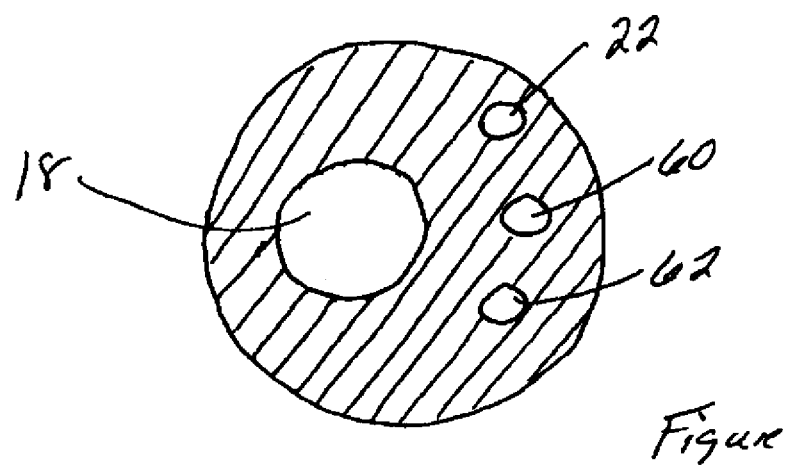
FIG. 5B is a diagrammatic view of a portion of a thrombectomy apparatus in accordance with an embodiment of the invention.

FIGS. 5A and 5B are schematic cross-sectional views providing several examples of how the elongate shaft 12 could accommodate the actuation filament 50 and the wire 52. FIG. 5A provides an example in a wire lumen 58 extends through the elongate shaft 12 and is parallel with the evacuation lumen 18 and the high pressure lumen 22. The wire lumen 58 may be sized to accommodate both the actuation filament 50 and the wire 52. In some instances, the wire lumen 58 may have a diameter that is large enough to permit relative axial movement between the actuation filament 50 and the wire 52 yet small enough to limit relative radial movement between the actuation filament 50 and the wire 52.

FIG. 5B provides an example in which an actuation filament lumen 60 and a wire lumen 62 extend through the elongate shaft 12 and are parallel with the evacuation lumen 18 and the high pressure lumen 22. The actuation filament lumen 60 may be sized to slidingly accommodate the actuation filament 50 and the wire lumen 62 may be sized to slidingly accommodate the wire 52. While FIGS. 5A and 5B show the additional lumens as being formed within a single shaft, it will be recognized that one or more of wire lumen 58, actuation filament lumen 60 and wire lumen 62 may be formed within distinct and separate tubular members that may be joined together to form the elongate shaft 12.

Figure 6:
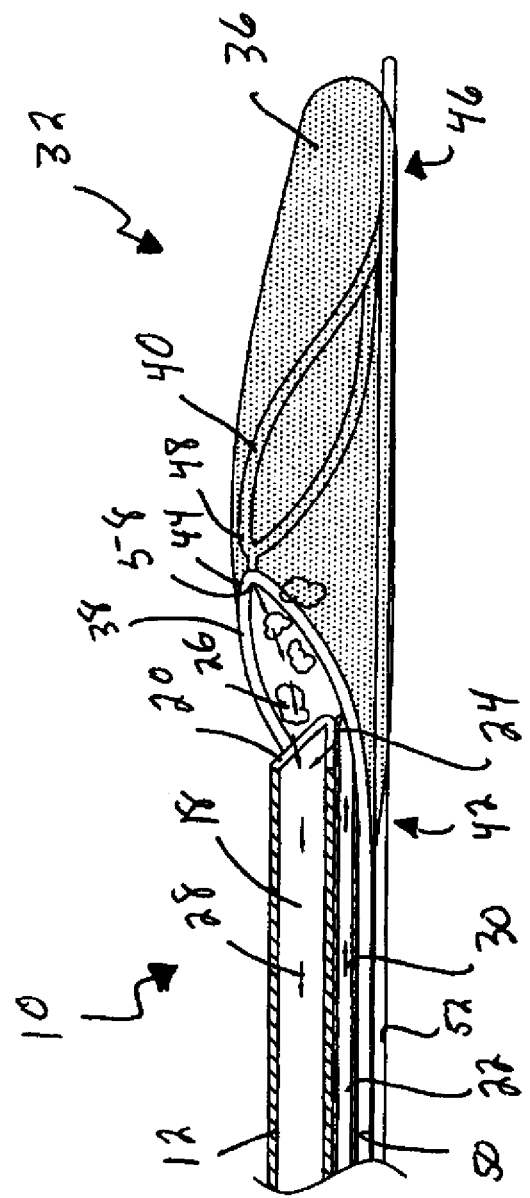
FIG. 6 is a diagrammatic view of a portion of a thrombectomy apparatus in accordance with an embodiment of the invention.

FIG. 6 is similar to FIG. 5, but adds a high pressure jet 58 located near the distal end 44 of the first loop 38. In some cases, the high pressure jet 58 may simply be a small aperture formed within a tube forming the first loop 38, particularly if the tube forming the first loop 38 is hollow and is in fluid communication with a high pressure fluid source such as the high pressure lumen 22. In some instances, it is contemplated that the high pressure jet 58 may be an orifice provided in a separate fluid line (not illustrated).

As illustrated, the high pressure jet 58 may be considered as being pointed at least partially towards the distal opening 20 of the evacuation lumen 18. In some cases, the high pressure jet 58 may be pointed in a more downward direction. In some instances, the high pressure jet 58 may be aimed more directly at an interior surface of the membrane 36. In some cases, two, three or more high pressure jets such as high pressure jet 58 may be disposed at various locations in and near the expandable capture basket 32.

Figure 7:
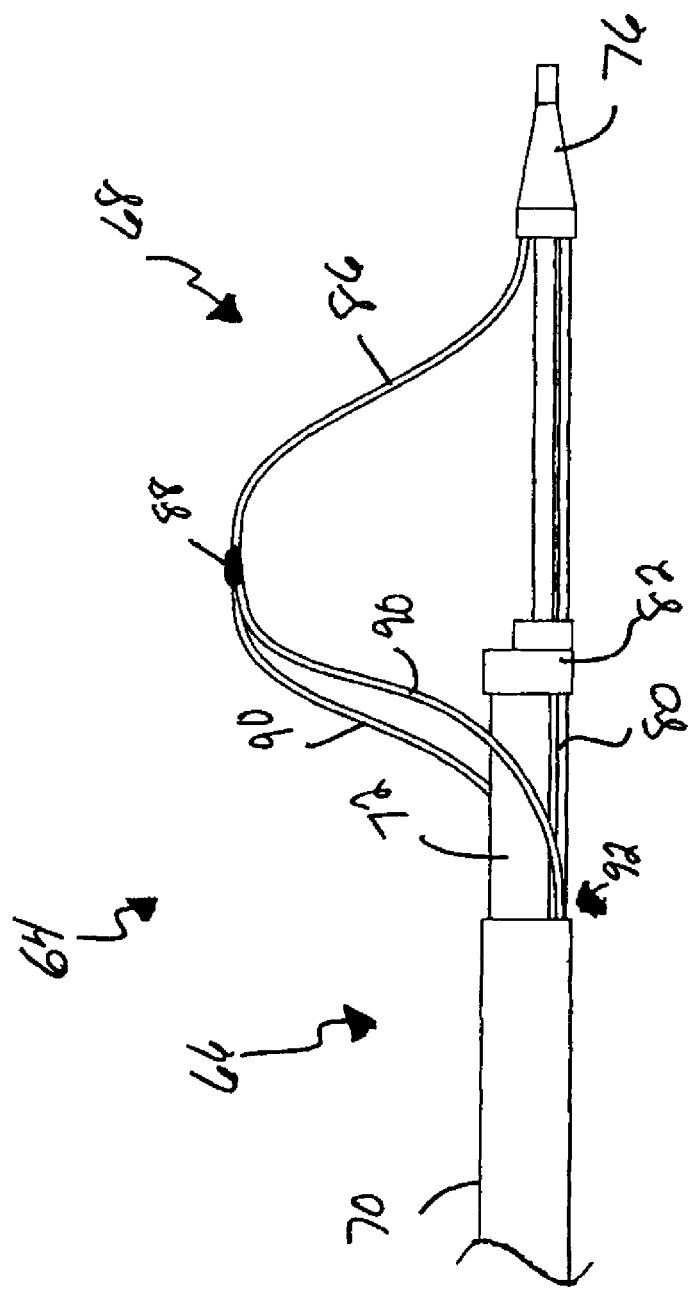
FIG. 7 is a diagrammatic view of a portion of a thrombectomy apparatus in accordance with an embodiment of the invention.

FIG. 7 provides an illustrative thrombectomy apparatus 64 that is configured to provide pressurized fluid to one or more locations within a capture basket. The thrombectomy apparatus 64 includes a catheter portion 66 and a basket portion 68. The catheter portion 66 includes a proximal shaft section 70 and an intermediate shaft section 72 that is disposed at least partially within the proximal shaft section 70 and extends distally therefrom. A distal shaft section 74 extends from the intermediate shaft section 72 and extends distally to a distal tip 76. It will be recognized that the catheter portion 66 may include one or more lumens such as an evacuation lumen, a high pressure fluid lumen, wire lumen, guidewire lumen, and the like.

The proximal shaft section 70 and the intermediate shaft section 72 may be configured to provide an evacuation lumen similar to the evacuation lumen 18 previously discussed. An evacuation lumen may, for example, terminate at a distal opening 78. As discussed previously, the evacuation lumen (not seen in this view) may be placed in fluid communication with a low pressure source such as suction to draw thrombi and other unwanted material into the evacuation lumen.

A proximal high pressure fluid line 80 may extend parallel to the intermediate shaft section 72. The proximal high pressure fluid line 80 may extend proximally within the proximal shaft section and may be in fluid communication with a high pressure fluid source. The proximal high pressure fluid line 80 may extend to a junction 82, from which a distal high pressure fluid line 84 may extend distally to the distal tip 76. If desired, the junction 82 may include a jet orifice, but this is not required.

For clarity, the basket portion 68 is shown without a membrane, but it will be recognized that the basket portion 68 may include a membrane similar to the membrane 36 described previously with respect to FIG. 2. The basket portion 68 includes a tubular line 86 that extends proximally from the distal tip 76. In some instances, the distal tip 76 may include appropriate plumbing connections such that the tubular line 86 may be in fluid communication with the distal high pressure fluid line 84. In some cases, the tubular line 86 may extend to a junction 88. If desired, the junction 88 may also include a jet orifice.

A pair of actuation filaments 90 are connected to the junction 88 and extend proximally therefrom. In some cases, the actuation filaments 90 enter the proximal shaft section 70 via an entrance 92 and extend proximally through the proximal shaft section 90. By moving the actuation filaments 90 in an axial direction, the basket portion 68 may be moved between an open configuration (as illustrated) and a closed configuration. In some instances, the actuation filaments 90 may be wires. In some cases, one or both of the actuation filaments 90 may be hollow tubes that may be in fluid communication with the junction 88.

FIGS. 8 through 13 provide illustrative but non-limiting examples of thrombectomy apparatuses. For clarity, certain elements such as wire lumens and capture basket membranes are excluded from the drawings. It will be recognized, however, that these elements may be included, as desired.

Figure 8:
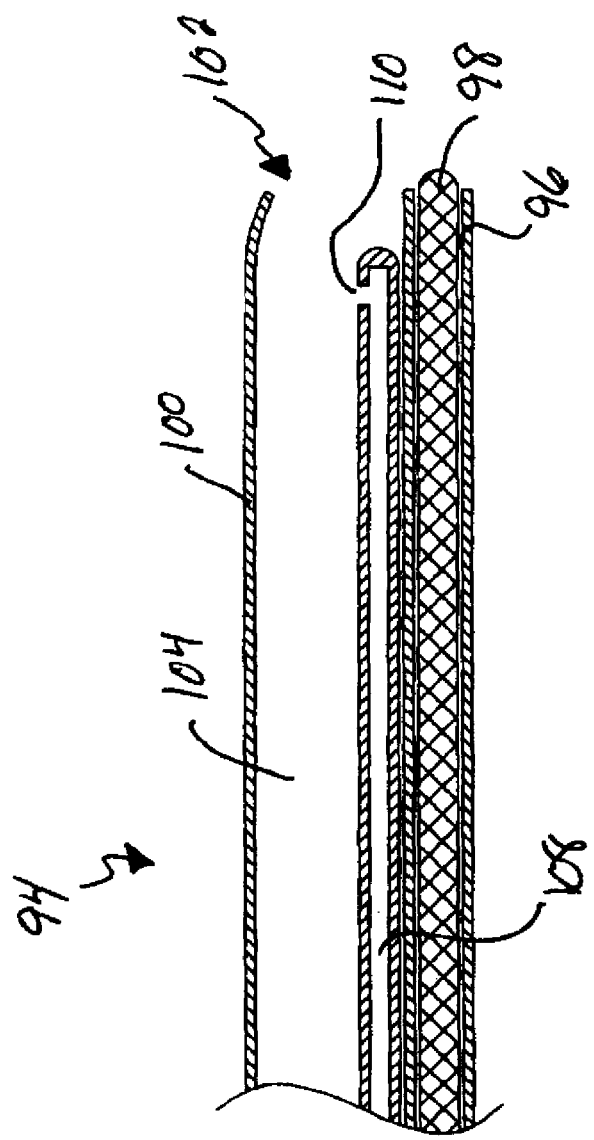
FIG. 8 is a diagrammatic view of a portion of a thrombectomy apparatus in accordance with an embodiment of the invention.

FIG. 8 shows a thrombectomy apparatus 94 that may be either a monorail or an over-the-wire type. The thrombectomy apparatus 94 includes a guidewire lumen 96 through which a guidewire 98 is disposed. While only a distal portion of the guidewire lumen 96 is seen in the Figure, one of skill will recognize that the guidewire lumen 96 may have a relatively short length if the thrombectomy apparatus 94 is intended as a monorail (or single-operator exchange) catheter. In some instances, the guidewire lumen 96 may extend a substantial distance proximally if the thrombectomy apparatus 94 is designed as an over-the-wire catheter.

The thrombectomy apparatus 94 includes an elongate shaft 100 extending to a distal end 102. The guidewire lumen 96 may, if desired, be formed as an integral portion of the elongate shaft 100. An evacuation lumen 104 is formed within the elongate shaft 100 and extends distally to a distal opening 106. The evacuation lumen 104 may be in fluid communication with a low pressure source such as vacuum. In some instances, as illustrated, the distal opening 106 may be tapered to facilitate advancement of the thrombectomy apparatus 94 through a patient's vasculature, for example, yet still be sized appropriate to accommodate thrombi and other similar material.

The elongate shaft 100 also includes a high pressure lumen 108 that extends distally within the elongate shaft 100. The high pressure lumen 108 includes a jet orifice 110 that is disposed in a side of the high pressure lumen 108 proximate a distal end thereof. It can be seen that in this configuration, the jet orifice 110 may provide a fluid jet that traverses the evacuation lumen 104 and thus may help break up any thrombi passing into the evacuation lumen 104.

Figure 9:
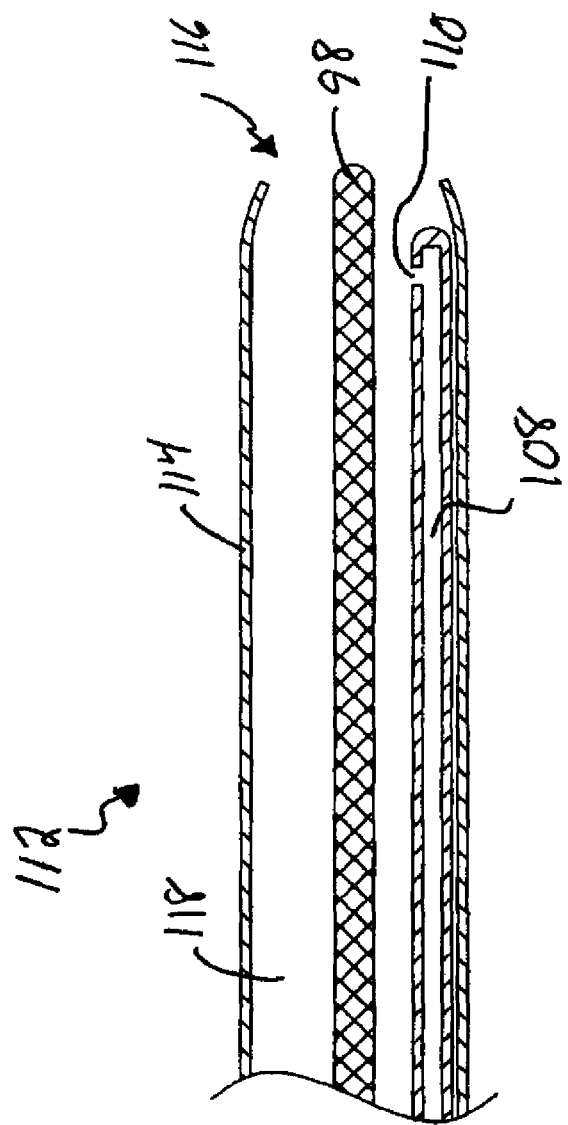
FIG. 9 is a diagrammatic view of a portion of a thrombectomy apparatus in accordance with an embodiment of the invention.

FIG. 9 shows a thrombectomy apparatus 112 that is configured as an over-the-wire type. The thrombectomy apparatus 112 includes an elongate shaft 114 extending to a distal end 116. An evacuation lumen 118 is formed within the elongate shaft 114 and extends distally to a distal opening 120. A guidewire 98 extends through the evacuation lumen 118.

The evacuation lumen 118 may be in fluid communication with a low pressure source such as vacuum. In some instances, as illustrated, the distal opening 120 may be tapered to facilitate advancement of the thrombectomy apparatus 112 through a patient's vasculature, for example, yet still be sized appropriate to accommodate thrombi and other similar material.

The elongate shaft 101140 also includes a high pressure lumen 108 that extends distally within the elongate shaft 100. The high pressure lumen 108 includes a jet orifice 110 that is disposed in a side of the high pressure lumen 108 proximate a distal end thereof. It can be seen that in this configuration, the jet orifice 110 may provide a fluid jet that traverses the evacuation lumen 118 and thus may help break up any thrombi passing into the evacuation lumen 118.

Figure 10:
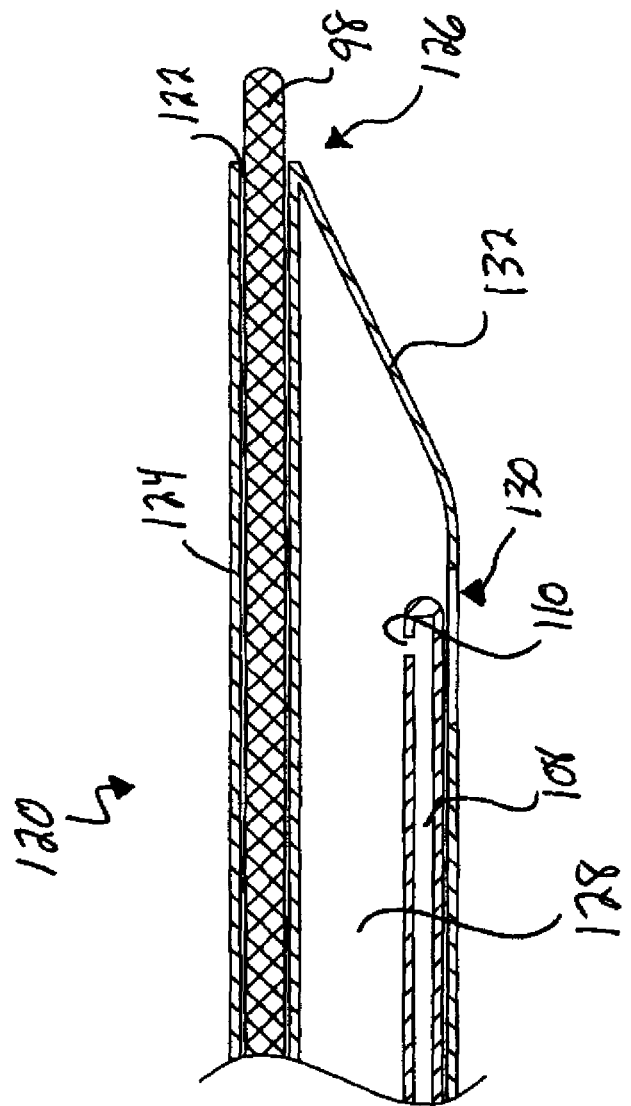
FIG. 10 is a diagrammatic view of a portion of a thrombectomy apparatus in accordance with an embodiment of the invention.

FIG. 10 shows a thrombectomy apparatus 120 that may be either a monorail or an over-the-wire type. The thrombectomy apparatus 120 includes a guidewire lumen 122 through which a guidewire 98 is disposed. While only a distal portion of the guidewire lumen 122 is seen in the Figure, one of skill will recognize that the guidewire lumen 122 may have a relatively short length if the thrombectomy apparatus 120 is intended as a monorail (or single-operator exchange) catheter. In some instances, the guidewire lumen 122 may extend a substantial distance proximally if the thrombectomy apparatus 120 is designed as an over-the-wire catheter.

The thrombectomy apparatus 120 includes an elongate shaft 124 extending to a distal end 126. The guidewire lumen 122 may, if desired, be formed as an integral portion of the elongate shaft 124. An evacuation lumen 128 is formed within the elongate shaft 124 and extends distally. In some cases, as illustrated, the evacuation lumen 128 may have a side opening 130 that is sized to permit thrombi and similar material to enter the evacuation lumen 128 through the side opening 130. The evacuation lumen 128 may be in fluid communication with a low pressure source such as vacuum. In some instances, as illustrated, the elongate shaft 124 may terminate in an angled end 132 to facilitate advancement of the thrombectomy apparatus 120 through a patient's vasculature, for example.

The elongate shaft 124 also includes a high pressure lumen 108 that extends distally within the elongate shaft 124. The high pressure lumen 108 includes a jet orifice 110 that is disposed in a side of the high pressure lumen 108 proximate a distal end thereof. It can be seen that in this configuration, the jet orifice 110 may provide a fluid jet that traverses the evacuation lumen 128 and thus may help break up any thrombi passing into the evacuation lumen 128. In this configuration, the jet orifice 110 may be positioned at or near a midpoint of the side opening 130.

Figure 11:
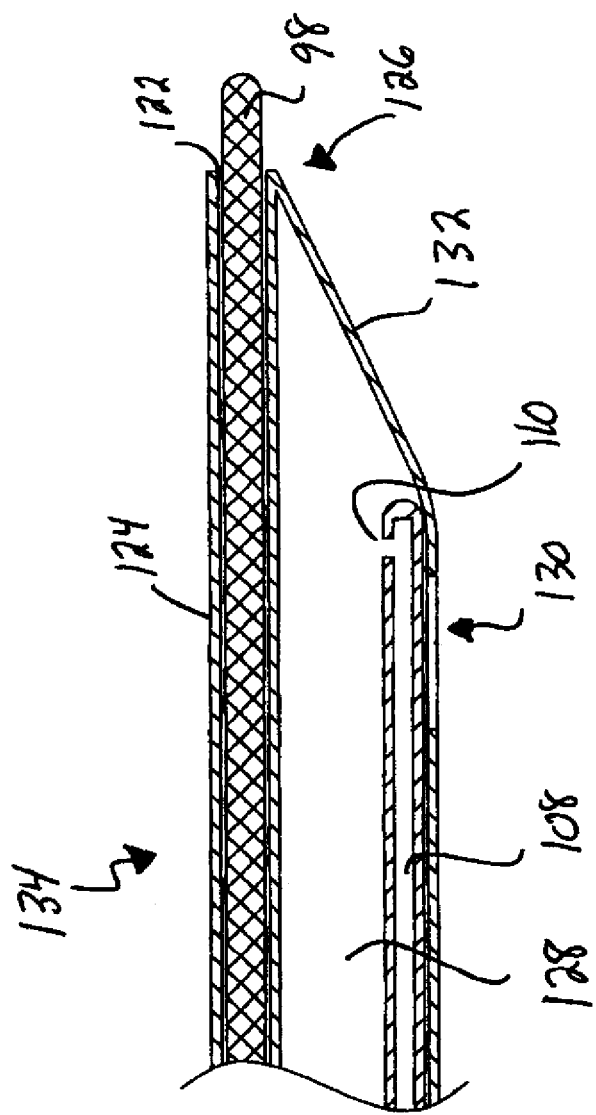
FIG. 11 is a diagrammatic view of a portion of a thrombectomy apparatus in accordance with an embodiment of the invention.

FIG. 11 shows a thrombectomy apparatus 134 that may be either a monorail or an over-the-wire type. The thrombectomy apparatus 134 includes a guidewire lumen 122 through which a guidewire 98 is disposed. While only a distal portion of the guidewire lumen 122 is seen in the Figure, it will be recognized that the guidewire lumen 122 may have a relatively short length if the thrombectomy apparatus 134 is intended as a monorail (or single-operator exchange) catheter. In some instances, the guidewire lumen 122 may extend a substantial distance proximally if the thrombectomy apparatus 134 is designed as an over-the-wire catheter.

The thrombectomy apparatus 134 includes an elongate shaft 124 extending to a distal end 126. The guidewire lumen 122 may, if desired, be formed as an integral portion of the elongate shaft 124. An evacuation lumen 128 is formed within the elongate shaft 124 and extends distally. In some cases, as illustrated, the evacuation lumen 128 may have a side opening 130 that is sized to permit thrombi and similar material to enter the evacuation lumen 128 through the side opening 130. The evacuation lumen 128 may be in fluid communication with a low pressure source such as vacuum. In some instances, as illustrated, the elongate shaft 124 may terminate in an angled end 132 to facilitate advancement of the thrombectomy apparatus 134 through a patient's vasculature, for example.

The elongate shaft 124 also includes a high pressure lumen 108 that extends distally within the elongate shaft 124. The high pressure lumen 108 includes a jet orifice 110 that is disposed in a side of the high pressure lumen 108 proximate a distal end thereof. In this configuration, the jet orifice 110 may be positioned at or near a distal edge of the side opening 130.

Figure 12:
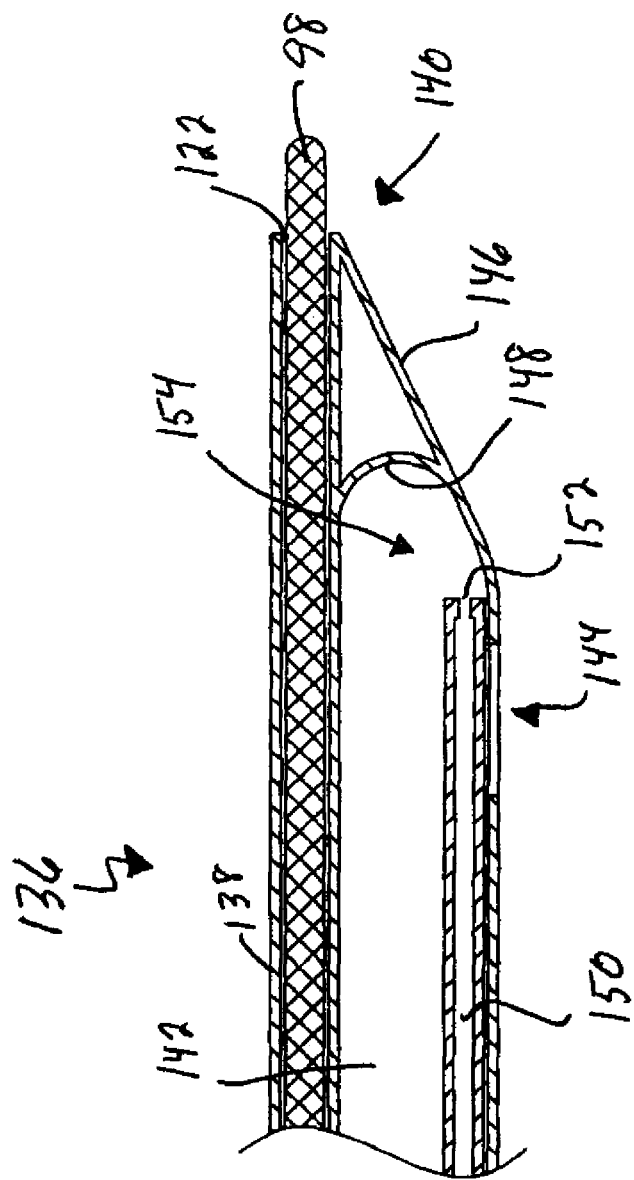
FIG. 12 is a diagrammatic view of a portion of a thrombectomy apparatus in accordance with an embodiment of the invention.

FIG. 12 shows a thrombectomy apparatus 136 that may be either a monorail or an over-the-wire type. The thrombectomy apparatus 136 includes a guidewire lumen 122 through which a guidewire 98 is disposed. While only a distal portion of the guidewire lumen 122 is seen in the Figure, one of skill will recognize that the guidewire lumen 122 may have a relatively short length if the thrombectomy apparatus 136 is intended as a monorail (or single-operator exchange) catheter. In some instances, the guidewire lumen 122 may extend a substantial distance proximally if the thrombectomy apparatus 136 is designed as an over-the-wire catheter.

The thrombectomy apparatus 136 includes an elongate shaft 138 extending to a distal end 140. The guidewire lumen 122 may, if desired, be formed as an integral portion of the elongate shaft 124. An evacuation lumen 142 is formed within the elongate shaft 124 and extends distally. In some cases, as illustrated, the evacuation lumen 142 may have a side opening 144 that is sized to permit thrombi and similar material to enter the evacuation lumen 142 through the side opening 144. The evacuation lumen 142 may be in fluid communication with a low pressure source such as vacuum. In some instances, as illustrated, the elongate shaft 138 may terminate in an angled end 146 to facilitate advancement of the thrombectomy apparatus 136 through a patient's vasculature, for example. In some cases, the angled end 146 may include an interior curved surface 148, if desired to control flow characteristics within the evacuation lumen 142.

The elongate shaft 138 also includes a high pressure lumen 150 that extends distally within the elongate shaft 138. The high pressure lumen 150 includes a jet orifice 152 that is disposed in a distal end of the high pressure lumen 150. It can be seen that in this configuration, the jet 152 110 may provide a fluid jet that can cause turbulence within a distal region 154 of the evacuation lumen 142. In some cases, this turbulence may help break up any thrombi passing into the evacuation lumen 142.

Figure 13:
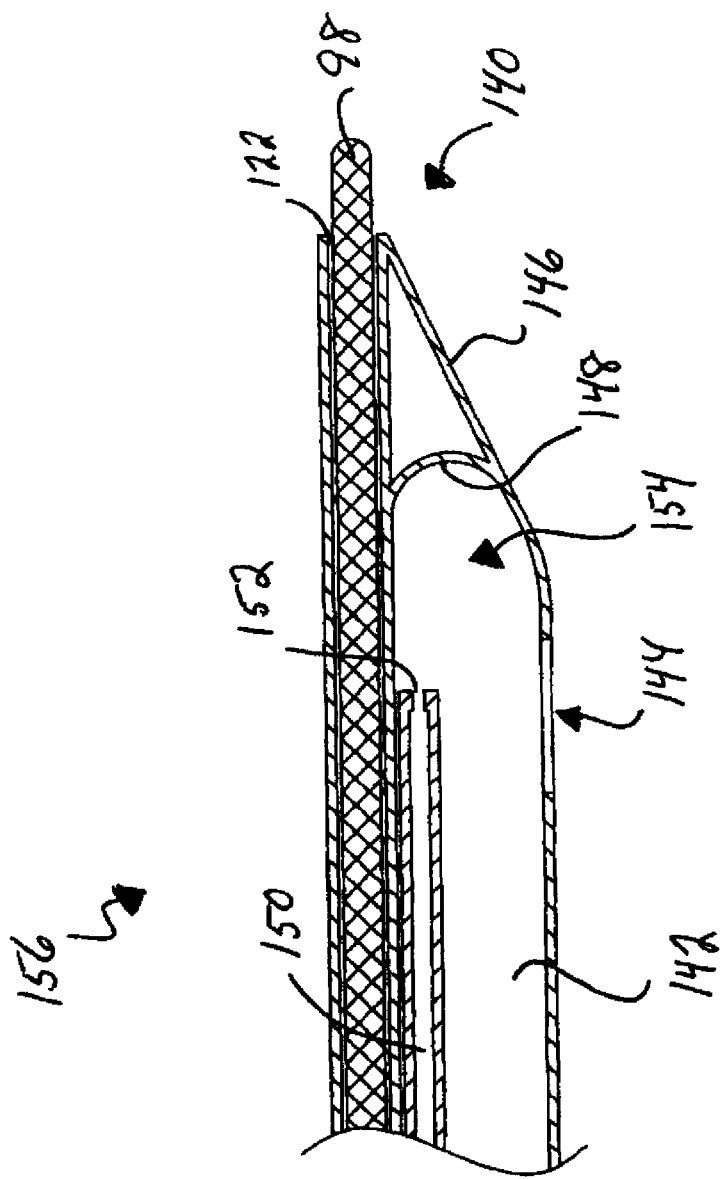
FIG. 13 is a diagrammatic view of a portion of a thrombectomy apparatus in accordance with an embodiment of the invention.

FIG. 13 shows a thrombectomy apparatus 156 that may be either a monorail or an over-the-wire type. The thrombectomy apparatus 156 includes a guidewire lumen 122 through which a guidewire 98 is disposed. While only a distal portion of the guidewire lumen 122 is seen in the Figure, one of skill will recognize that the guidewire lumen 122 may have a relatively short length if the thrombectomy apparatus 156 is intended as a monorail (or single-operator exchange) catheter. In some instances, the guidewire lumen 122 may extend a substantial distance proximally if the thrombectomy apparatus 156 is designed as an over-the-wire catheter.

The thrombectomy apparatus 156 includes an elongate shaft 138 extending to a distal end 140. The guidewire lumen 122 may, if desired, be formed as an integral portion of the elongate shaft 124. An evacuation lumen 142 is formed within the elongate shaft 124 and extends distally. In some cases, as illustrated, the evacuation lumen 142 may have a side opening 144 that is sized to permit thrombi and similar material to enter the evacuation lumen 142 through the side opening 144. The evacuation lumen 142 may be in fluid communication with a low pressure source such as vacuum. In some instances, as illustrated, the elongate shaft 138 may terminate in an angled end 146 to facilitate advancement of the thrombectomy apparatus 156 through a patient's vasculature, for example. In some cases, the angled end 146 may include an interior curved surface 148, if desired to control flow characteristics within the evacuation lumen 142.

The elongate shaft 138 also includes a high pressure lumen 150 that extends distally within the elongate shaft 138. Unlike FIG. 12, in FIG. 13 the high pressure lumen 150 is located away from the side opening 144. The high pressure lumen 150 includes a jet orifice 152 that is disposed in a distal end of the high pressure lumen 150. It can be seen that in this configuration, the jet 152 110 may provide a fluid jet that can cause turbulence within a distal region 154 of the evacuation lumen 142. In some cases, this turbulence may help break up any thrombi passing into the evacuation lumen 142.

Figure 14:
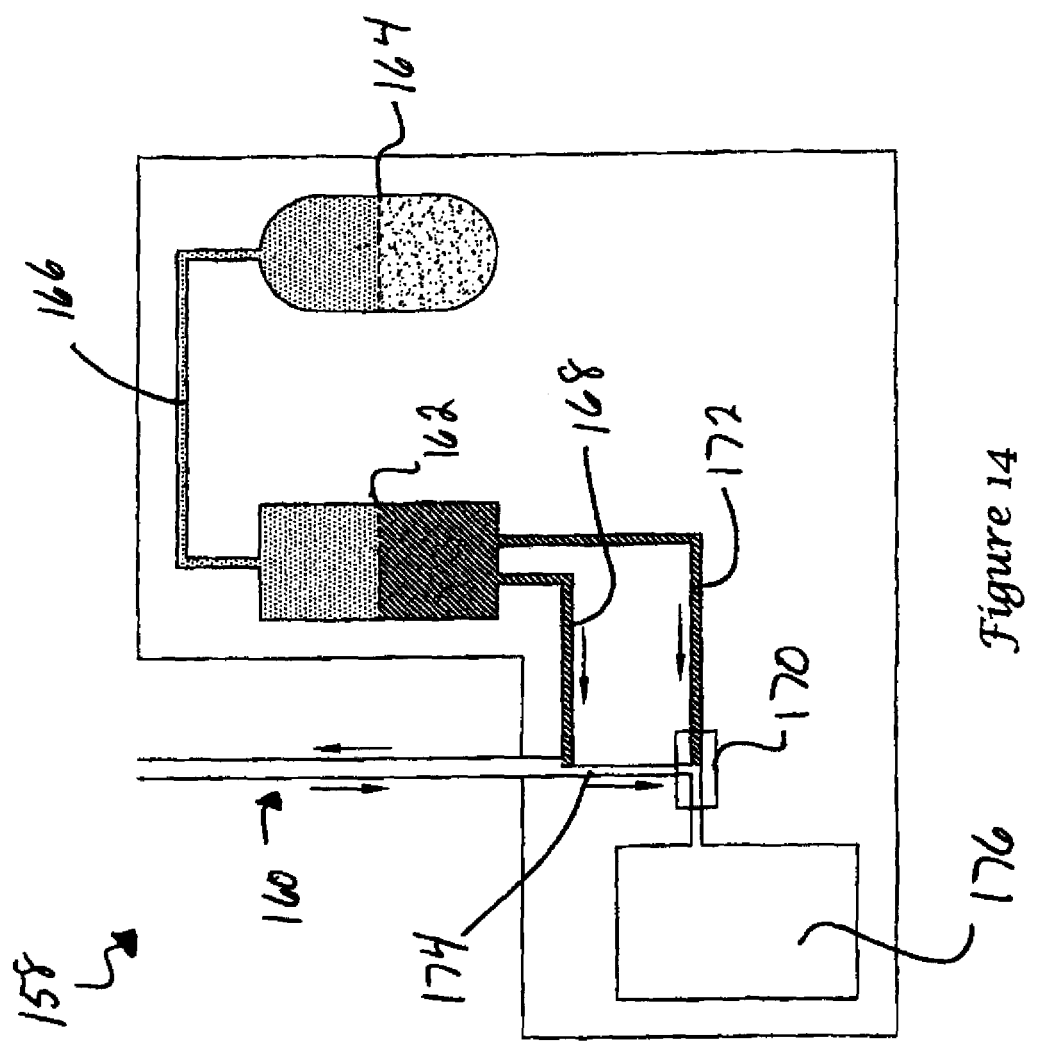
FIG. 14 is a diagrammatic view of a thrombectomy system in accordance with an embodiment of the invention.

FIG. 14 schematically illustrates a thrombectomy system 158. In some cases, the thrombectomy system 158 may be considered as being a self-contained assembly that can be operated without exterior fluid or power connections. The thrombectomy system 158 includes a thrombectomy apparatus 160, similar to those described above with respect to FIGS. 1 through 13. A working fluid reservoir 162 may be pressurized via a propellant that is stored within a propellant reservoir 164.

In some cases, the propellant reservoir 164 may contain a propellant in liquid form. As the propellant vaporizes, the resultant gas may travel through a line 166 and into the working fluid reservoir 162. As diagrammatically illustrated, the propellant reservoir 164 may be about half full with a liquefied propellant (bottom half as drawn) and about half full with a vaporized propellant. Similarly, the bottom half of the working fluid reservoir 162 may be filled with a liquid working fluid such as saline while the top half is filled with the vaporized propellant. In some cases, the propellant is carbon dioxide. As a result, the working fluid in working fluid reservoir 162 is pressurized as the propellant in propellant reservoir 164 vaporizes. Alternatively, it is contemplated that the working fluid may be pressurized externally. For example, an external source of a pressurized gas such as oxygen or nitrogen could be used to pressure the working fluid within the working fluid reservoir 162.

Pressurized working fluid may be provided to the thrombectomy apparatus 160 via a supply line 168. In some cases, pressurized working fluid may also be provided to a suction device 170 via another supply line 172. The suction device 170 may, for example, be a jet pump suction device, a venture, or the like, and may be connected to a low pressure lumen within the thrombectomy apparatus 160 via supply line 174. In some cases, it is contemplated that suction may instead be provided externally, such as a vacuum port within a hospital room, for example. Any thrombi or other material removed via the thrombectomy apparatus 160 may be collected in a collection reservoir 176. In some cases, the collection reservoir 176 may be a reusable container. In some instances, the collection reservoir 176 may be a disposable bag or other similar structure.

Figure 15:
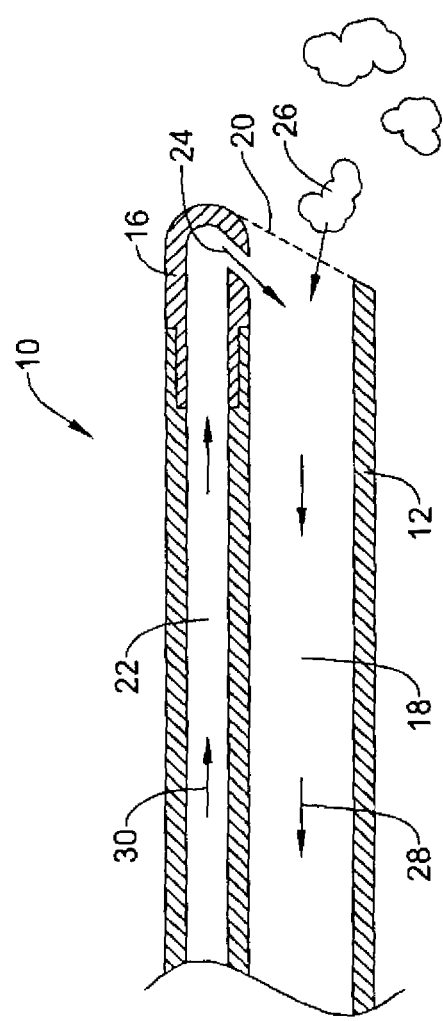
FIG. 15 is a diagrammatic view of a thrombectomy system in accordance with an embodiment of the invention.

FIG. 15 shows a thrombectomy apparatus which may function without an associated capture device. Thrombectomy catheter 10 includes an elongate shaft 12 having an evacuation lumen 18 and a generally parallel high pressure lumen 22. The elongate shaft 12 optionally may accommodate the high pressure lumen 22, a guide wire lumen (not shown) and the like as shown in FIG. 5A. In other embodiments, the high pressure lumen 22 may be provided as a distinct and separate tubular member that may be joined to the evacuation lumen 18 to form elongate shaft 12. The evacuation lumen 18 may terminate at a distal opening 20. The high pressure lumen 22 may terminate near the distal opening 20 of elongate shaft 12 at a distal opening 24. In some embodiments, the distal opening 24 may be formed in a distal plug 16 inserted in the high pressure lumen 22. Thrombi 26, generically shown disposed just distal of the distal opening 20 of elongate shaft 12, may be drawn into evacuation lumen 18 by providing a low pressure source to a proximal end (not illustrated) of the evacuation lumen 18. In some embodiments a suitable fluid such as a saline or other therapeutically acceptable fluid may travel in a direction indicated by arrow 30 within high pressure lumen 22. Upon exiting distal opening 24, the flow may join a flow existing within evacuation lumen 18 generally in the direction of arrow 28. In some configurations, especially when the flow exiting distal opening 24 is directed generally between perpendicular to the axis of the low pressure lumen 18 and axially within the low pressure lumen in the direction indicated by arrow 30, the flow exiting distal opening 24 may provide an ejector/aspirator action to assist in drawing thrombus 26 within elongate shaft 12. It is believed that the flow exiting distal opening 24 may disrupt and dilute thrombus as it enters evacuation lumen 18.

In some cases, parts or all of the devices described herein may be doped with, made of, coated with, or otherwise include a radiopaque material. Radiopaque materials are understood to be materials capable of producing a relatively bright image on a fluoroscopy screen or another imaging technique during a medical procedure. Some examples of radiopaque materials can include, but are not limited to, gold, platinum, palladium, tantalum, tungsten alloy, polymer material loaded with a radiopaque filler, and the like.

In some instances, a degree of MRI compatibility may be imparted into parts of the devices described herein. For example, to enhance compatibility with Magnetic Resonance Imaging (MRI) machines, it may be desirable to make various portions of the devices described herein from materials that do not substantially distort MRI images or cause substantial artifacts (gaps in the images). Some ferromagnetic materials, for example, may not be suitable as they may create artifacts in an MRI image. In some cases, the devices described herein may include materials that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some instances, some of the devices described herein may include a coating such as a lubricious coating or a hydrophilic coating. Hydrophobic coatings such as fluoropolymers provide a dry lubricity. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

What is claimed is:

1. A thrombectomy system comprising: an elongate catheter shaft configured to be inserted within a patient's vasculature and comprising a low pressure lumen comprising a proximal end and a distal end, the distal end forming an opening; a tubular member comprising a proximal end and a distal end and comprising a high pressure lumen comprising a proximal end and a distal end, the tubular member extending within the low pressure lumen, wherein the high pressure lumen is closed at its distal end by a plug inserted into the high pressure lumen, and wherein the tubular member has an opening disposed near its distal end which communicates between the high pressure lumen and the low pressure lumen, and which is in proximity to the opening of the low pressure lumen; and wherein the opening of the tubular member is configured to cause fluid supplied through the high pressure lumen from a high pressure source to exit from the opening of the tubular member at a high rate of speed capable of breaking thrombi within the low pressure lumen into smaller pieces when the proximal end of the low pressure lumen is coupled to a vacuum source.

2. The thrombectomy system of claim 1, further comprising a guidewire lumen associated with the elongate catheter shaft, the guidewire lumen configured for accommodating a guidewire.

3. The thrombectomy system of claim 2, wherein the guidewire lumen has a relatively short length compared to the elongate catheter shaft.

4. The thrombectomy system of claim 1, further comprising an expandable capture basket.

5. The thrombectomy system of claim 1, wherein the opening of the low pressure lumen is substantially perpendicular to a longitudinal axis of the elongate catheter shaft.

6. The thrombectomy system of claim 1, wherein the opening of the low pressure lumen is obliquely oriented with respect to a longitudinal axis of the elongate catheter shaft.

7. The thrombectomy system of claim 1, wherein the fluid exiting from the opening of the tubular member traverses the low pressure lumen.

8. The thrombectomy system of claim 1, wherein the fluid exiting from the opening of the tubular member comprises at least one jet.

9. A thrombectomy system comprising: an elongate catheter shaft configured to be inserted within a patient's vasculature and comprising a low pressure lumen comprising an axis and a proximal end and comprising a distal end which forms an opening; a tubular member comprising a proximal end and a distal end and comprising a high pressure lumen comprising a proximal end and a distal end, the tubular member extending within the low pressure lumen, wherein the high pressure lumen is closed at its distal end by a plug inserted into the high pressure lumen and wherein the tubular member has an opening disposed near its distal end which communicates between the high pressure lumen and the low pressure lumen, the opening located in proximity to the opening of the low pressure lumen; and wherein the opening of the tubular member is configured to cause fluid supplied through the high pressure lumen from a high pressure source to exit from the opening of the tubular member as at least one jet directed generally between a direction perpendicular to the axis of the low pressure lumen and a direction along the axis of the low pressure lumen away from the distal end of the low pressure lumen and toward the proximal end of the low pressure lumen when the proximal end of the low pressure lumen is coupled to a vacuum source.

10. The thrombectomy system of claim 9, further comprising a guidewire lumen associated with the elongate catheter shaft, the guidewire lumen configured for accommodating a guidewire.

11. The thrombectomy system of claim 10, wherein the guidewire lumen has a relatively short length compared to the elongate catheter shaft.

12. The thrombectomy system of claim 9, further comprising an expandable capture basket.

13. The thrombectomy system of claim 9, wherein the at least one jet traverses the low pressure lumen.

14. The thrombectomy system of claim 9, wherein the at least one jet comprises a plurality of jets.

15. The thrombectomy system of claim 9, wherein the opening of the low pressure lumen is substantially perpendicular to a longitudinal axis of the elongate catheter shaft.

16. The thrombectomy system of claim 9, wherein the opening of the low pressure lumen is obliquely oriented with respect to a longitudinal axis of the elongate catheter shaft.

* * * * *